United States Patent [19]

Nagasaki et al.

[11] Patent Number: 4,638,353
[45] Date of Patent: Jan. 20, 1987

[54] ILLUMINATING MEANS FOR COLOR IMAGE SENSING

[75] Inventors: Tatsuo Nagasaki, Musashino; Hiroyoshi Fujimori, Hachioji, both of Japan

[73] Assignee: Olympus Optical Co., Ltd., Tokyo, Japan

[21] Appl. No.: 647,520

[22] Filed: Sep. 5, 1984

[30] Foreign Application Priority Data

Sep. 5, 1983 [JP] Japan ................................. 58-163582
Sep. 5, 1983 [JP] Japan ................................. 58-163583
Sep. 5, 1983 [JP] Japan ................................. 58-163584

[51] Int. Cl.⁴ .......................... A61B 1/04; A61B 1/06; H04N 7/18; H04N 9/07
[52] U.S. Cl. ......................................... 358/98; 128/6; 358/42
[58] Field of Search ..................... 358/98, 42; 128/4–8, 128/303, 15; 350/96, 26; 356/241

[56] References Cited

U.S. PATENT DOCUMENTS

Re. 31,290 6/1983 Moore ..................................... 358/98
2,721,893 10/1955 Vanderhooft .......................... 358/42

FOREIGN PATENT DOCUMENTS 53-90685 8/1978 Japan .
58-43686 3/1983 Japan .

Primary Examiner—Howard W. Britton
Attorney, Agent, or Firm—Armstrong, Nikaido, Marmelstein & Kubovcik

[57] ABSTRACT

Image Sensing means are provided in a solid-state image sensing element at the focus of an imaging optical system, as well as elements for illuminating a sequential three color mode, or the like comprising three color filters each transmitting light having each different wave length along the optical path between said solid-state image sensing element and a light source. Light transmitting elements are provided including liquid crystal panel wherein light transmitting portions are successively switched by applying a voltage so as to pass successively each color filter portions or alternately light transmitting elements are provided wherein the positions of light transmitting portions are successively switched with respect to said color filter portions by displacing reciprocally the light transmitting means to enable the color image sensing.

11 Claims, 18 Drawing Figures

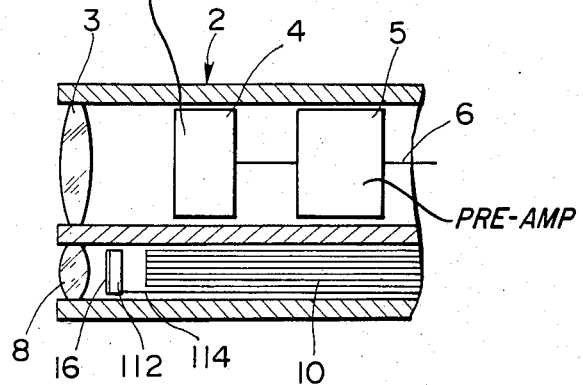
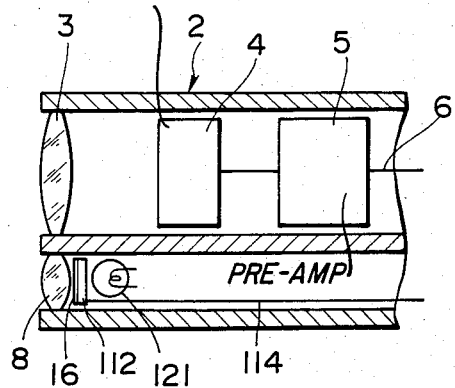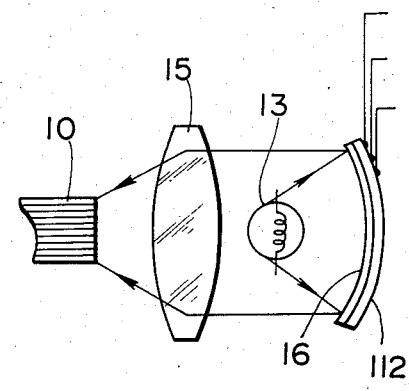

ILLUMINATING MEANS FOR COLOR IMAGE SENSING

BACKGROUND OF THE INVENTION

This invention relates to illuminating means for color imaging sensing means for sensing the image of a diseased part or the like polychromatically by an endoscope assembly. Imaging sensing means have been employed using solid state image sensing elements for television cameras, endoscope assemblies, etc. Conventional endoscope assemblies employ so-called "image guide" and "light guide" comprising bundles of optical fibers, for example, several thousand of optical filaments, each having a diameter of several ten microns as image transferring means and light transferring means. In particular, in an endoscope assembly, a sensed image of an object to be observed is focussed at the tip of an image guide inserted from the operational trailing end to the vicinity of object by means of a focussing optical system (i.e. optical sensing system), transmitted to the trailing end and observed by means of an optical eyepiece system.

On the other hand, in an endoscope assembly employing said solid state image sensing element, it is preferable to display the image polychromatically in order to improve the visual diagnosis. Generally known means for providing color images include a combination of a color splitting optical system and three monochromatic solid state sensing means elements, or a combination of single solid-state image sensing element and a mosaic filter having a great number of red, green and blue color elements.

The former system has a disadvantage in that it is difficult to arrange a color splitting optical system and a plurality of solid-state image sensing elements in the thin and small space of an endoscope assembly. The latter system has also a disadvantage in that since light split into three colors is received, only ⅓ of the members in said solid-state image sensing element are allotted to each color, thereby reducing the resolving power when compared with that for a monochromatic image. Further, because the receiver elements for each color don't receive light at the same position, the colors are mixed insufficiently thus resulting in insufficient color matching.

For these reasons, in a prior art publication as disclosed in Published Japanese patent application No. 43686/1983, a plurality of light-reflecting means having selectivity of wave length such as dichroic mirrors are attached to the light source means at a suitable angles with regard to the illuminating optical system to provide light deflecting means for reflecting the illuminating light from the light source by means of said light-reflecting means to be guided to the light guide. Thus, the illumination successively of light of red, green and blue color is sensed by monochromatic solid state image sensing elements and stored in synchronized with the illumination in each frame memory or the like. These signals are read concurrently from these frame memories during regeneration to provide a color image.

In the above prior art, the arrangement of each dichroic mirror and optical deflector system, etc. is complicated and needs various adjustments and is therefore expensive and unsuitable for the mass production. The arrangement has low mechanical strength and said optical systems tend to be biased even by a small impact or the like such that a decrease in the illuminating light intensity and degradation in the color registration by the higher bias may result.

Moreover, in prior art as disclosed in Published Japanese patent application No. 90685/1978, three color filters are rotated by a motor to illuminate the three primary colors successively by a time division system. In this prior art, the filter should be rotated at a substantially high rate of rotation for regenerating one frame in 30 seconds as so images on conventional color televisions, which rate of revolution requires a relatively large motor. If the number of color filters attached to the supporter disk are increased, the rate of rotation may be reduced but the load is therefore increased excessively to cause the motor to overload.

As in the prior art when the filters are rotated by means of a motor, the motor is not incorporated in a small space. In addition, the motor issues noise having varied frequency causing an adverse effect on the vicinity. The mechanisms as illustrated by the above-mentioned prior art may be employed as illuminating means but not as image sensing means.

SUMMARY OF THE INVENTION

It is a primary object of this invention to provide illuminating means for providing a color image without degrading the resolving power.

It is another object of this invention to provide illuminating means for providing a color image capable of being incorporated into a relatively small space.

It is a further object of this invention to provide illuminating means for providing a color image and applicable within a wide range.

Other features and advantages of this invention will be seen sufficiently by the following description.

BRIEF DESCRIPTION OF DRAWINGS

FIG. 16 is a sectional view of a tip of an insert member of an endoscope assembly according to an eighth embodiment of the instant invention;

FIG. 17 is a sectional view of a tip of an insert member of an endoscope assembly according to a ninth embodiment of the instant invention; and FIG. 18 is a schematic view of essential members in a tenth embodiment of the instant invention.

DETAILED DESCRIPTION OF PREFERRED EMBODIMENTS

Figure 1:
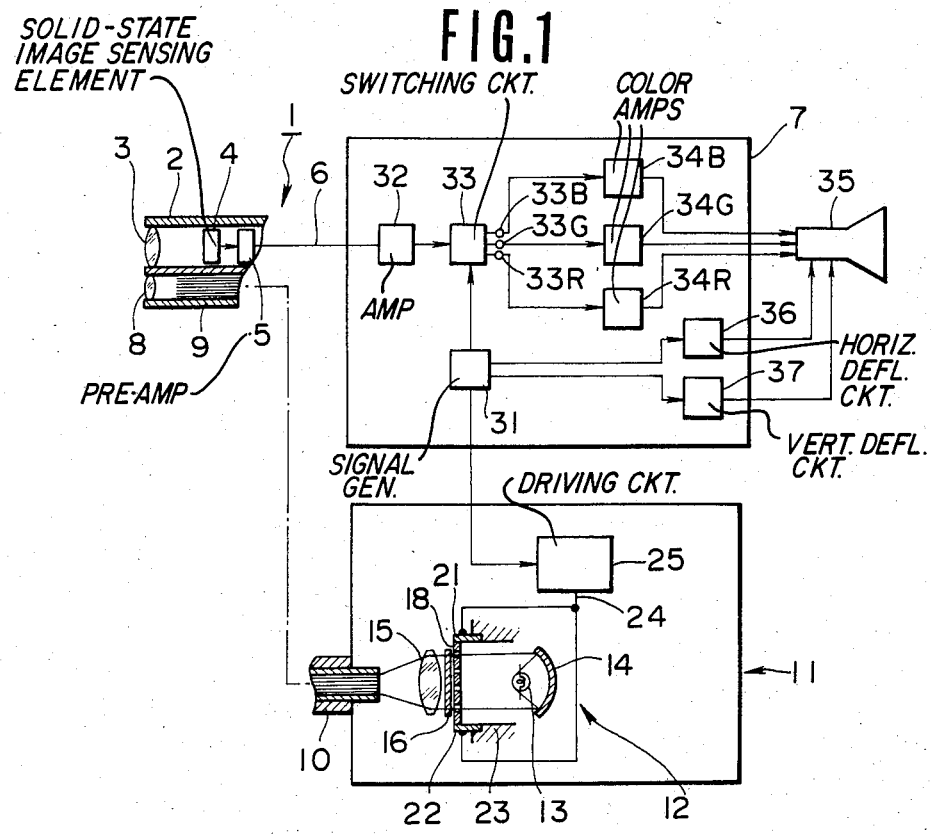
FIG. 1 is a schematic view of an endoscope assembly according to a first embodiment of the instant invention.

As shown in FIG. 1, the endoscope assembly 1 is provided with an elongated and flexible insert member 2 and a focussing objective lens system 3 at the tip of insert member 2. A solid-state image sensing element 4 is positioned in the focal plane of objective lens system 3. On the rear side of solid-state image sensing element 4, a preamplifier 5 is incorporated for amplifying the output signal from said solid-state image sensing element 4 with a low noise factor. The output signals from the preamplifier 5 are applied through lead wire bundle 6 to the operational means at the accessible trailing end of endoscope assembly 1 or to the video-processor means 7 installed separately.

Figure 4:
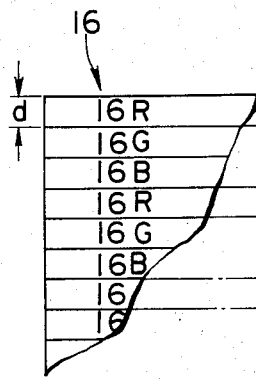
FIG. 4 is a front enlarged view of a portion of three primary color filters of the embodiment of FIG. 1.
Figure 5:
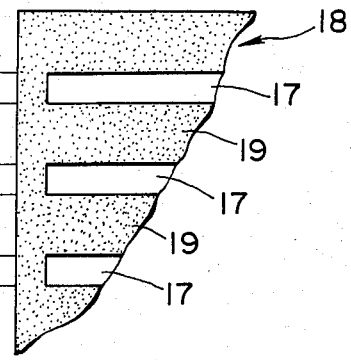
FIG. 5 is a front view of a shutter disk of the embodiment of FIG. 1.

A light distributing lens system 8 is attached to illuminating opening provided in the vicinity of said objective lens system 3 in said insert member 2. A light guide 9 comprising optical fibre bundles for transmitting the illuminating light is inserted through insert member 2 so that the tip of light guide is placed within said light distributing lens system 8. Said light guide 9 is inserted through the flexible light guide cable and a connector 10 is formed at the trailing end of insert member 2 to be attached detachably to light source means 11. The end surface of the light guide attached to connector 10 is irradiated successively with illuminating light of monochromatic color changing alternatively. Illuminating means 12 sequentially projects three primary colors and each monochromatic light incident onto said end surface and through said light distributing lens system 8 to illuminate an object to be viewed as shown in the enlarged view of FIG. 2. In said illustrating means 12, the light projected from incandescent lamp 13 is turned to parallel light flux by means of a concave mirror 14, focussed through condensor lens 15 and passed through a three color filter 16 as shown in FIG. 4. The light also passes through shutter disk 18 provided with light transmitting slits 17 in registration with the stripes provided in filter 16 as shown in FIG. 5, the shutter disk 18 being positioned in the optical path between lamp 13 and the incident end of light guide 9. Said three color filter 16 comprises successively arranged red transmitting filters 16R, green transmitting filters 16G and blue transmitting filters 16B each for passing therethrough a stripe having a width of d of light having a corresponding wave length.

Figure 2:
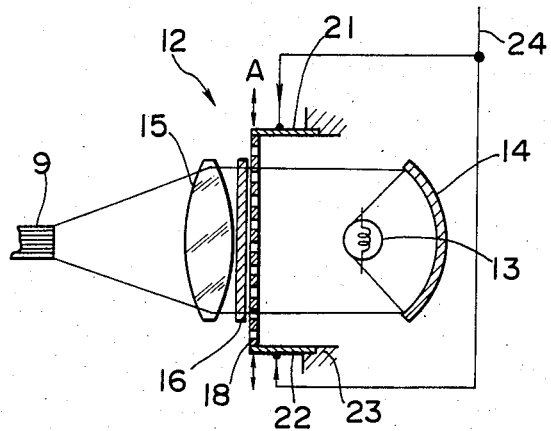
FIG. 2 is an outlined sectional view of illuminating means of the first embodiment.
Figure 3:
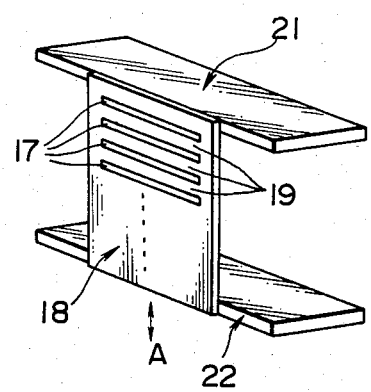
FIG. 3 is a prespective view of a shutter disk and bi-morph oscillator for driving the shutter disk.

On the other hand, shutter disk 18 is provided with light transmitting slits 17 having a width slightly narrower than distance d in registration with said stripes and elongated shutter lands 19 each having a width of 2×d. In short, the shutter disk 18 exclusively guides light passing through each light transmitting slit 17 to color transmitting filters opposing each light transmitting slit 17. As shown in FIGS. 2 or 3, the upper and lower ends of said shutter disk 18 are attached with the legs of bi-morph vibrators 21, 22, another legs of bi-morph vibrators 21, 22 being secured to framework 23.

Said bi-morph vibrators 21, 22 are supplied with, for example, saw-toothed or stepwise driving voltage from bi-morph vibrator driving circuitry 25 through lead wires 24 to be displaced vertically downwards and upwards within the same phase, in other words to the direction perpendicular to the longitudinal direction of slits as shown by arrows A in FIGS. 2 and 3 by the applied voltage and the object is irradiated by red, green and blue light respectively at a displacement of zero, d and 2×d.

Said driving circuitry 25 is supplied with switching signals from color switching signal generator circuitary 31 for generating switching signals for changing over the image signals under the illumination with each color to regenerate the signals in video-processor means 7 and issue voltage of saw-toothed or other form in synchronization with the switching signals.

In said video-processor means 7, the output signals from solid-state image sensing element 4 are amplified through preamplifier 5 and then further amplified through amplifier 32.

The incorporation of said preamplifier 5 within the tip of insert member 2 is intended not to damp the SN ratio by the damping through lead wire bundle 6 and the like or by noise entrained midway.

The output from said amplifier 32 is supplied to signal switching circuitary 33 to issue 3 color signals successively to color signal output terminals 33R, 33G, 33B by changing over the multiplexer or the like. The color signals applied to color signal output terminals 33R, 33G, 33B are amplified sufficiently through color amplifier circuitary 34R, 34G, 34B and applied on each grid of color cathode-ray tube 35. In such a case, color switching signal generator circuitary 31 supplies the output signals for the color switching to horizontal deflection circuitary 36 and vertical deflection circuitary 37 to generate each horizontal deflection signal and vertical deflection signal. The horizontal and vertical deflection outputs generated in circuits 36, 37 sweep the electron beams of color cathode-ray tube 35 to form successively the color image by the three color signals.

The display frequencies of three colors have periods faster than the time of residual image so as to be observed visually as a colored image.

In the endoscope assembly equipped with illuminating means 12 projecting three-color sequential light constructed according to the first embodiment, three color filters 16 and shutter disk 18 are arranged in closely opposing relation in the optical path between incandescent lamp 13 and condensor lens 15. For example, at the pupillary position of lens 15 shutter disk 18 is displaced reciprocally by applying a voltage of saw-toothed wave form or other form to bi-morph vibrators 21, 22. Before the displacement of shutter disk 18, each light transmitting slit 17 is positioned in the opposing relationship with red transmitting filter 16R so that red light is transmitted exclusively through the slits to illuminate the object. The image signals received by solid-state image sensing element 4 and amplified through preamplifier 5 and amplifier 32 during this interval are transmitted through color signal switching circuitry 33 to red light amplifier circuitry 34R to display the red image on color cathode-ray tube 35 while being swept by horizontal and vertical deflection outputs. When said shutter disk 18 is displaced downwards by about d, signal switching circuitry 33 is connected to green signal output terminal 33G and the image signals received by solid-state image sensing element 4, converted to electrical signals and supplied during this interval are amplified through green color amplifier circuitry 34G to display similarly green images on color cathode-ray tube 35. When shutter disk 18 is displaced downwards by about 2×d, the illuminating light is turned to blue and the blue image is displayed on the tube depending on the light intensity received by solid-state image sensing element 4.

Shutter disk 18 displaced downwards by about 2×d is returned quickly to the original position at the steep descending portion of saw tooth wave form and the above-mentioned motions are repeated.

The image displayed by three colors on said color cathode-ray tube 35 is observed as a colored image.

According to the first embodiment functioning as mentioned above, the object can be illuminated successively by the three color by limiting the width d of stripe of three colors filter 16 to a sufficiently small value and forming the light transmitting slits 17 of shutter disk 18 correspondingly and by reciprocating shutter disk 18 in a small amplitude by applying a voltage on bi-morph vibrators 21, 22. A thin metal panel may be fabricated into shutter disk 18 having a number of light transmitting slits 17 by etching or the like to provide a light weight and small sized shutter disk. (The shutter disk 18 may also be formed by coating or printing a light-blocking paint on a transparent disk.) Accordingly, the small-sized and light weight shutter disk can be driven sufficiently by small bi-morph vibrators 21, 22 and with reduced power consumption. It has a simple structure and can be manufactured by mass production with reduced cost. It has also relatively high mechanical strength.

In addition, said driving circuit 25 is designed to apply saw-toothed wave forms on bi-morph vibrators 21, 22. But it is more effective to apply a voltage of stepwise wave of 0, d, 22×d, 0, . . . to displace the shutter disk to each predetermined position in a short time and, after a duration sufficient to allow reception of picture elements required for providing an image from solid-state image sensing element 4 to displace the shutter disk quickly to the subsequent position.

Figure 6:
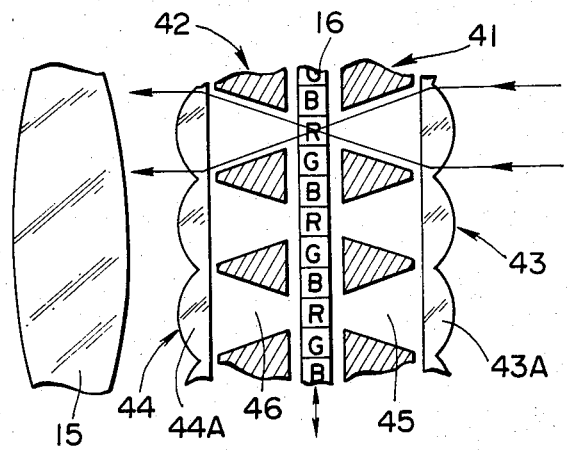
FIG. 6 is a sectional view of essential members in a second embodiment.

FIG. 6 illustrates essential members in a means for illuminating successively light of three colors according to the second embodiment of this invention.

This embodiment is intended to improve the utilisation efficiency of light quantity.

In FIG. 6, shutter disk 41, 42 are provided at both sides of three color filter 16 according to the first embodiment and shutter disks 41, 42 are sandwiched, in turn, between flyeye lens system 43, 44, thereby forming means for guiding illuminating light to each light transmitting filter by displacing the three color filter.

Shutter disks, 41, 42 each have a number of light transmitting slits 45, 46, having each slit a decreasing width to a point nearest the three color filter 16 where the width is d. The widest outside end opposes the crowned portion of corresponding cylindrical lens 43A, 44A of flyeye lens system 43, 44. As shown by the arrows, the illuminating light incident from the incandescent lamp is converged through each cylindrical lens 43A of flyeye lens system 43, passed through apertures 45, filtered through three color filter 16, passed through aperture 46 and converged through flyeye lens system 44 to parallel light. In this embodiment, three color filter 16 is displaced reciprocally by means of bi-morph vibrators as referred to hereinbefore.

Figure 7:
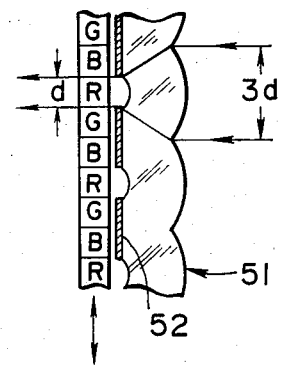
FIG. 7 is a sectional view of essential members in a third embodiment.

According to this embodiment, the illuminating light can be utilised substantially completely so as to improve the illuminating efficiency. The intensity of light is, for example, three times as great as that in the first embodiment. FIG. 7 illustrates essential parts in the third embodiment of this invention.

While the second embodiment employs 2 flyeye lens systems 43, 44, this embodiment employs single flyeye lens system 51 at the side of incandescent lamp. Flyeye lens system 51 converges light incident with a width of 3×d to the inside concave portions having a width of d to issue parallel light to three color filter 16.

The zones of flyeye lens system 51 defined by two vicinal concave portions having a width of about d at the side of three color filter 16 comprise light blocking zones of light blocking film 52 formed by coating a light blocking paint thereon or the like.

The third embodiment functions similarly to the second embodiment and has advantages that only one flyeye lens system 51 is employed and that the light blocking zones can be formed integrally by coating a light blocking paint on the rear surface of flyeye lens system 51, thereby saving the production costs.

In this embodiment, three color filter 16 is also driven by the bi-morph vibrators.

Figure 8:
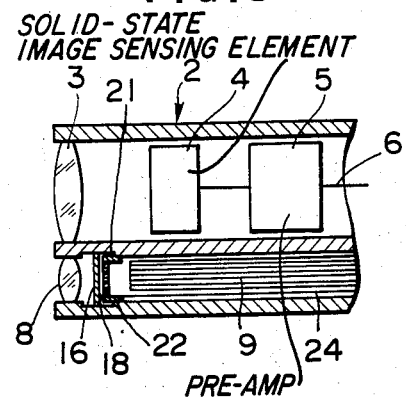
FIG. 8 is a sectional view of essential members in a fourth embodiment.

FIG. 8 illustrates the tip of insert member of an endoscope assembly according to the fourth embodiment of this invention.

In this embodiment, bi-morph vibrators 21, 22 are not installed within light source means 11 but at the tip of insert member 2. Namely, there are provided three color filter 16, shutter disk 18 and bi-morph vibrators 21, 22 for driving shutter disk 18 to be reciprocated, all of which are structured similarly to the first or other embodiment at positions between the leading end of light guide 9 and light distributing lens system 8 at the tip of insert member 2.

As seen from this embodiment, the means according to this invention can be incorporated into a significantly small space.

In addition, high performance luminous diodes or a lamp may be employed in lieu of said light guide 9.

Figure 9:
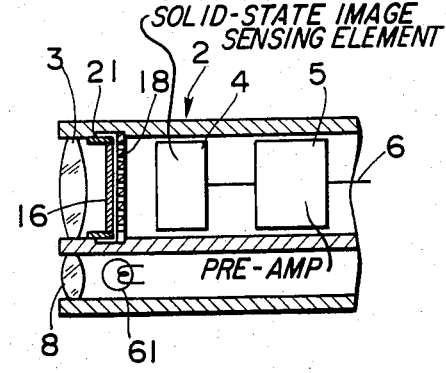
FIG. 9 is a sectional view of essential members in a fifth embodiments.

FIG. 9 illustrates the fifth embodiment of this invention wherein image sensing means are provided with successive light of three color images at the light receiver side. In this embodiment, there are provided three color filter 16 having a structure similar to that of the first or other embodiment, shutter disk 18 provided with a number of light transmitting slits and bi-morph vibrators 21, 22 at the emergent pupilary position of objective lens system 3 before the leading end of solid-state image sensing element 4. Bi-morph vibrators 21, 22 are designed to displace three color filter 16 reciprocally.

According to this embodiment, the object is illuminated continuously by light having at least three wave lengths of three colors issued from, for example, incandescent lamp 6. The light reflected from said object is passed through three color filter 16 and shutter disk 18 displaced reciprocally by the vibrators and light having wave lengths of three colors is successively transmitted and focussed on the image sensing plane (focal plane) of solid-state image sensing element 4.

Consequently, a color image can be displayed by supplying the signals from each receiver element of solid-state image sensing elements 4 during the focussing with each color.

According to the fifth embodiment, a color image can be displayed by applying the embodiment not only to an endoscope assembly but also to monochromatic image sensing means under normal illumination. In such a case, three color filter 16 is of stripe type so as to be realized at lower costs than filter of mosaic type. While each color split through a mosaic filter cannot be incident upon the same receiver elements, each color splitted through the stripes of three color filter 16 by displacing reciprocally filter 16 can be incident to the same receiver elements so that the image having proper color registration is reproduced with fidelity. When the pickup member of solid-state image sensing element 4 comprises separately the receiver elements and transmitting means or the like, a decrease in the number of picture elements can be prevented by arranging each light transmitting slit compatibly to the arrangement of each receiver element and each light blocking zone compatibly to the arrangement of transmitting zone or the like between the receiver elements. When the width of a receiver element, d is substantially equal to that between two vicinal receiver elements in such a case, a decrease in the number of picture elements can be prevented by reducing the width of light transmitting zone to a value of smaller than d. When a receiver element is designed to be contacted with the vicinal receiver element, the number of picture elements can be maintained equally to that when the receiver elements receive monochromatic light by reducing further the width of light transmitting zones. In the above-mentioned embodiments, it is possible to replace the member to be displaced. For example, it is obvious in said first embodiment, three color filter 16 may be displaced reciprocally in lieu of shutter disk 18. Moreover, shutter disk 18 and three color filter 16 may be displaced in reversed phase.

The above embodiments employ bi-morph vibrators 21, 22 as displacing means. Such displacing means are not limited to such vibrator means and may be replaced by pieozoelectric vibrators or a combination of permanent magnet and solenoid or electromagnet.

Still further, it is obvious in the above embodiments to employ an incandescent lamp or high performance luminous diodes is lieu of light guide 9, provided that such a light source issues light including wave lengths of the three primary colors.

Still further, means for receiving signals of each picture element focussed on each receiver element of solid-state image sensing element 4 and displaying the signals on color cathode-ray tube 35 or liquid crystal display panel are not limited to one outline in the first embodiment. For example, the received signals are stored in frame memories or the like and displayed concurrently with three colors.

Still further, the present invention can be applicable not only to three color filter 16 and shutter disk 17 wherein the light transmitting zones comprise horizontally, vertically or obliquely elongated slits but also to a mosaic filter. The present invention is not limited to use light having wave lengths of three primary colors. As illuminating and -state image sensing means for displaying color images can be formed by using light including ranges of three different wave lengths, such mechanism should fall within the scope of present invention.

As mentioned above, the above mentioned embodiments are designed to transmit successively the light including wave length of each color by displacing a plurality of stripes of color transmitting filter or light guiding members so that color images having high resolving power can be realised employing monochromatic pickup element. The means according to the present invention are compact and light weight and have high durability and high mechanical strength.

Figure 10:
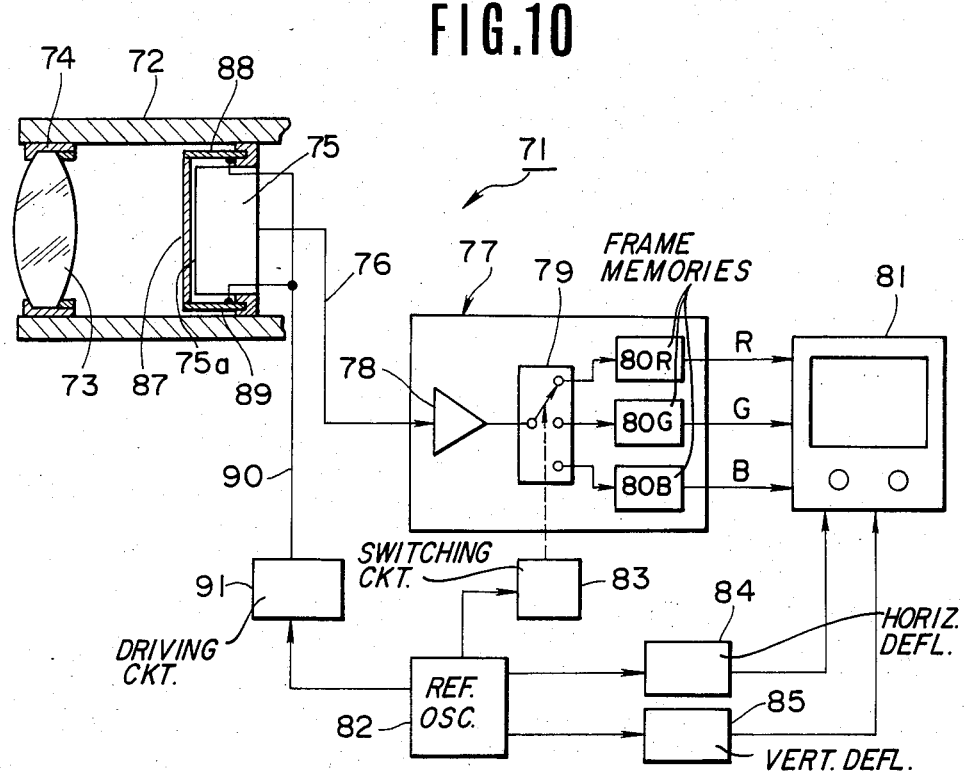
FIG. 10 is a schematic view illustrating the structure of a sixth embodiment of the instant invention.

FIG. 10 illustrates a color image sensing means according to the sixth embodiment of the present invention.

In color pickup means 71 of the sixth embodiment as shown in FIG. 10, an objective lens system 73 for picking up or focussing the image of an object is attached to cylindrical housing 72 at the opened leading end thereof via lens frame 74 and solid-state image sensing element 75 is arranged so that the image sensing surface 75a falls within the focal plane of said objective lens system 73 and is secured to the inner wall of cylindrical housing 72 via supporter means.

Said solid-state image sensing element 75 is designed to issue signals through lead wire 76 to amplifier 78 in signal processor means 77. The solid-state image sensing element is designed to be applied with clock signals for reading the signals corresponding to the picture elements through lead wire (not shown).

The output signals from said amplifier 78 are received successively through multiplexer 79 and transmitted to red, green and blue frame memories 80R, 80G, 80B to be stored. (When frame memories 80R, 80G, 80B are digital memories, the signals are A/D converted and stored in the memories.)

The signals stored in each frame memories 80R, 80G, 80B are read concurrently through each frame memories 80R, 80G, 80B, D/A converted and pass through color amplifier circuit (not shown) to be displayed on monitoring color cathode-ray tube 81.

For the clock or address type for reading the signals from said solid-state image sensing element 75, the address signals are formed based on the signals from reference oscillator 82 and said reference oscillator 82 successively switches multiplexer 79 through switching circuit 83 each when the signals corresponding each picture elements over one line to write the signals successively over one line to each frame memories 80R, 80G, 80B. The reference oscillator 82 supplies the address signals for writing to each address of said frame memories 80R, 80G, 80B through a frequency divider or the like and writes the address signals to each memory cell and the stored signals are read by the direction of said address signals and D/A converted and amplified. In addition, said reference oscillator 82 supplies reference signals to horizontal deflection circuit 84 and vertical deflection circuit 85 for generating saw-toothed horizontal and vertical deflection signals to be supplied to color cathode-ray tube 81 as sweeping signals.

On the other hand, there is arranged three color filter 87 comprising red transmitting filter 87R, green transmitting filter 87G and blue transmitting filter 87B for passing exclusively light having wave lengths of red, green and blue immediately before the focal plane 75a of said solid-state image sensing element 75. The upper and lower ends of three color filter 87 are secured to the leading ends of bi-morph vibrators 48, 49, the trailing ends of which are, in turn, secured to supporter means 76 secured to cylindrical housing 72. Each bi-morph vibrators 88, 89 are applied with driving voltage for vibrating the bi-morph vibrators in driving circuit 91 through lead wire 90.

Figure 11:
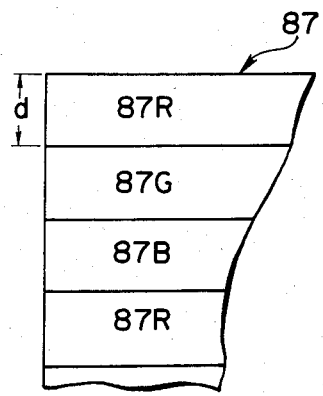
FIG. 11 is a front view of three-color filters employed in the embodiment of FIG. 10.
Figure 12:
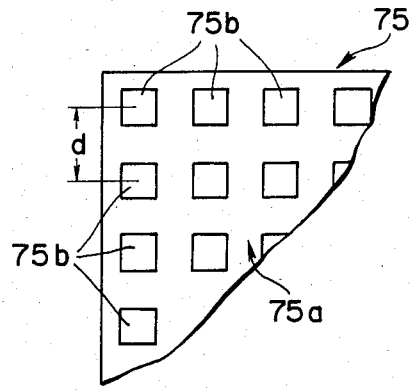
FIG. 12 is a front view showing the arrangement of receiver elements arranged on the focal plane of a solid-state image sensing element of the sixth embodiment of FIG. 10.

As shown in FIG. 11, said three color filter 87 comprises a number of selected color transmitting stripes 87R, 87G, 87B arranged repeatedly in order. As shown in FIG. 12, the width, d of each stripe is defined to be equal to the center distance between, say, horizontally vicinal receiver elements 75b, 75b for solid-state image sensing element 75, i.e., pitch of arranged receiver elements, d, as shown in FIG. 12.

Hence, when the image is focussed through objective lens system 73 and three color filter 87 under the deactuated condition on the focal plane 75a, receiver elements 75b, . . . , 75b receives optical images repeatedly in the order so that those at the uppermost row (1st line) receive the optical image of red wave length, those at the second row receive the optical image of green wave length, those at the third row receive the optical image of blue wave length, and so forth. Hence the image sensing operation is designed to be controlled so that the signals from receiver elements, 75b, . . . , 75b at each the corresponding lines are stored successively in each frame memories 80R, 80G, 80B through multiplexer 79 switched successively synchronized with each receiving interval for each lines.

After the completion of image sensing of the signals from receiver elements 75b, . . . , 75b from the uppermost row to the lowermost row, bi-morph vibrators 88, 89 are driven by the output from driving circuit 91 in synchronization with the completion of image sensing to displace three color filter 87 to the direction perpendicular to the direction of stripes, for example upwards by about d and the signals are again picked from receiver elements 75b, . . . , 75b at the uppermost row to those at the lowermost row. During this period, receiver elements 75b, . . . , 75b receive green image so that the signals are stored in green frame memory 80G and the signals from those at the second row are stored in blue frame memory 80B.

After the completion of image sensing of the signals from those at the lowermost row, bi-morph vibrators 88, 89 are displaced further upwards by a width of about d, the signals are picked up and stored in frame memory 80B from the blue image received by those at the uppermost row in a similar manner to that disclosed above.

After the completion of image sensing for those at the lowermost row, the voltage applied to bi-morph vibrators 88, 89 is turned to zero stepwise and the displacement of bi-morph vibrators 88, 89 is turned quickly to about zero to return the motion to the initial condition and repeat the above mentioned motions.

Thus the means are designed to sense the three color image stored in one frame without decreasing the number of picture elements from that in the monochromatic image by storing the signals from each receiver elements 75b, . . . , 75b correspondingly to the successive displacements of color filter 87 successively by zero, d, 2×d.

When the image is successively sensed in three colors and the signals for one frame as colored signals, i.e. totally for three frames are written, the signals are successively read from frame memories 80R, 80G, 80B, D/A converted, amplified, swept by the horizontal and vertical deflection outputs and displayed on monitoring color cathode-ray tube 11.

Hence, according to the sixth embodiment, each receiver element 75b receives successively light having wavelengths of three colors by displacing three color filter 87, thereby not degrading the resolving power and each light of the corresponding wave lengths and received successively each by the same receiver element 75b are mixed so that the color registration, etc. can be assured to reproduce the colored image of object with high fidelity.

Furthermore, there can be provided light-weight and small-sized three color filter 87 so as to be driven sufficiently by small bi-morph vibrators 88, 89.

Consequently, the driving means can be miniaturized so that it can be incorporated not only in a television camera, but also in a small space having a small diameter such as insert member of endoscope assembly.

Furthermore, since each filter, 87R, 87G, 87B is larger or wider than each receiver element 75b, they can function sufficiently without protruding by some overshooting when bi-morph vibrators 88, 89 are driven by a stepwise voltage or the like.

Still further, there can be designed a mechanism wherein a number of the receiver elements, say, 3 receiver elements capable to be functioned sufficiently at a high speed, say transversely on the focal plane 75a are arranged vertically at a pitch of d, a filter, say, a red transmitting filter is arranged before each of said receiver elements so that the switching signal is issued when the red light transmitted through red transmitting filter 87R of three color filter 87 displaced to the corresponding position overlapped with the red light transmitted through said additional red transmitting filter are received on said receiver elements. It is also possible in such a case to combine the synchronizing means with luminous element to assure the functioning without using external light.

In the preceding embodiment, three color filter 87 is displaced reciprocally, but similar effect can be achieved by displacing solid-state image sensing element 75, wherein the vertical address is changed depending on the bias per one or 2 pitches of arrangement or one pitch to the reversed direction by the displacement to store the bias in each memory cell in frame memories 80R, 80G, 80B. When the failure in the color registration is trifle, such calibration is not always necessary.

Still further, the functional effect similar substantially to the displacement of said solid-state image sensing element 75 can be achieved by displacing at least portionwise objective lens system 73, wherein the objective lens system 73 is not displaced vertically reciprocally, but preferably displaced so that the surface of lens system in parallel to the focal plane 75a is tilted slightly so as to bias the direction of light signal by one and two pitches or one and adverse pitches vertically (i.e. the direction perpendicular to the direction of stripes of three color filter 87) on the focal plane 75a.

Still further, substantially similar effect can be achieved by inserting not a transparent disk but a transparent prism member in the midway of the focussing optical system and displacing the prism member reciprocally to bias the optical path.

Still further, the color transmitting filter for color sensing is not limited to the three color filter but can be realized by three color filter for filtering light having varied ranges of wave length.

Figure 13:
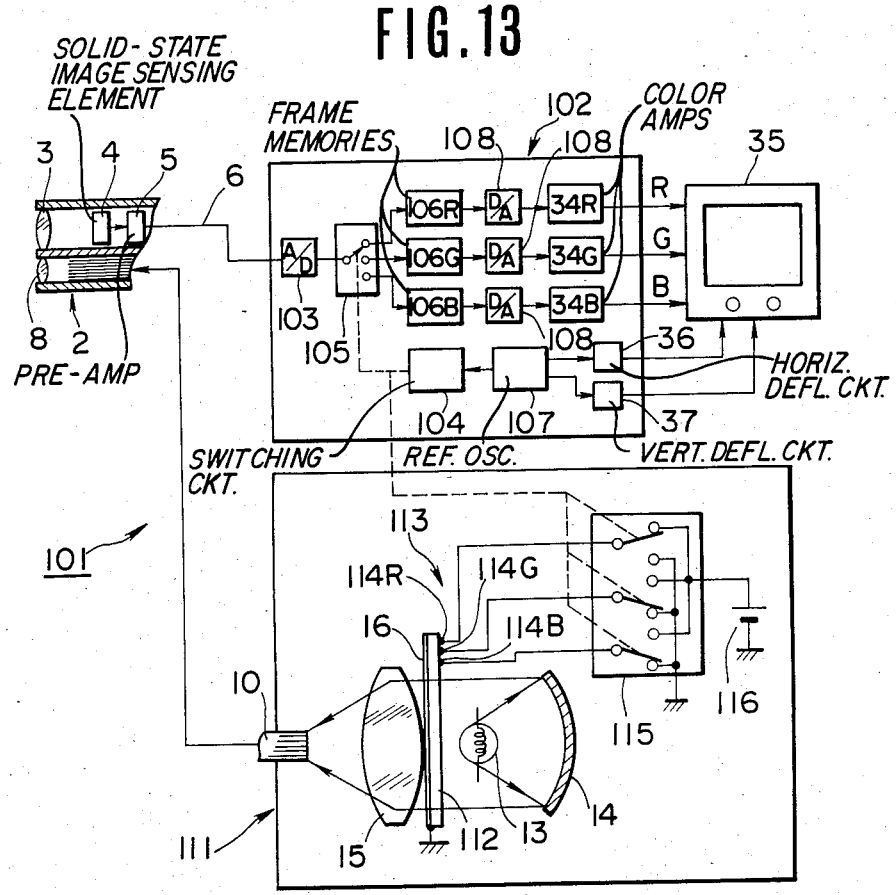
FIG. 13 is a schematic view showing fully the endoscope assembly equipped with a seventh embodiment of the instant invention.

FIG. 13 illustrate the seventh embodiment according to this invention wherein a liquid crystal is employed in lieu of the above-mentioned displacing means.

In this endoscope assembly 101, the output signals from preamplifier 5 are supplied to A/D converter 103 in video processor means 102 incorporated at the trailing processor means in endoscope assembly 101 or installed separately. The signals corresponding to the picture elements are converted dititally through A/D converter 103 and stored in red, green and blue frame memories 106R, 106G, 106B through multiplexer 105 which is switched by the switching signals issued from switching circuit 104. In addition, the digital data of three image signals (color signals) for one frame are stored successively in the frame memories turned to ON by multiplexer 105.

Said switching signals are formed by dividing the clock signals from reference oscillator 107, or the like and the clock signals are also used for the signals for sensing the signals from each receiver elements of solid-state image element 4.

Said reference oscillator 107 supplies the clock signals to an address generator circuit (not shown) to generate the address signal for assigning the address of memory cell for writing the signals to frame memories 106R, 106G, 106B and for assigning the reading address.

Moreover, said reference oscillator 107 supplied the clock signals in synchronization with the address signals for sensing from said frame memories 106R, 106G, 106B to horizontal and vertical deflection circuits, 36, 37 for issueing each horizontal and vertical deflection signals for applying these deflection outputs to the X- and Y-deflection terminals of color cathode-ray tube 35.

The digital picture element signals written in said frame memories 106R, 106G, 106B are read concurrently during the reading mode, converted through each D/A converter 108 to the respective digital signal to form color signals R, G, B. These color signals, R, G, B are amplified respectively through color amplifier circuits 34R, 34G, 34B and applied to color cathode ray tube (CRT) 35 and display three color images thereon while sweeping by the horizontal and vertical deflection signals.

The trailing end (incident end) of light guide 10 inserted through insert member 2 is designed to be attached to light source means 111.

In said light source means 111, a liquid crystal panel 112 is equipped in lieu of shutter disk 18 in the first embodiment.

In short, a three color filter 16 and a liquid crystal panel 112 in contact with one surface of said three color filter 16 are provided on the optical path between said condensor lens system 15 and illuminating lamp 13, for example, at the pupillary position of said condenser lens system 15 to form illuminating means 113 for sensing color images according to the seventh embodiment of the present invention as illustrated in FIG. 13.

Figures 14, 15:
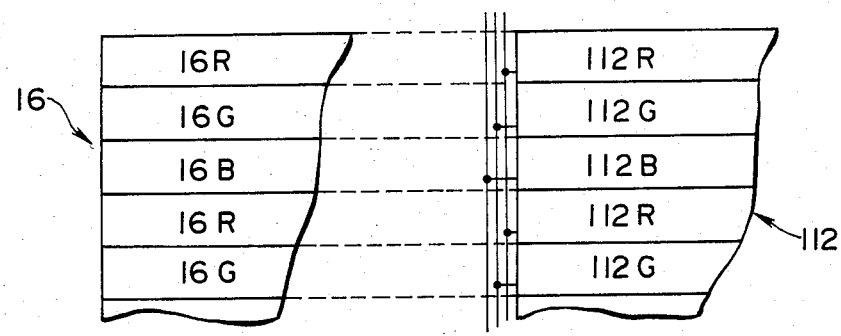
FIG. 14 is a front view of three color filter of the embodiment of FIG. 13.
FIG. 15 is a front view of shutter disk of the embodiment of FIG. 13.

Said three color filter 16 is formed by color filters 16R, 16G, 16B corresponding to red, green and blue respectively in stripe patterns as shown in FIG. 14.

Liquid crystal panel 112 is attached in contact with said three color filter 16 and comprises stripes 112R, 112G, 112B each corresponding to said filter 16R, 16G, 16B and which are converted to light transmitting stripes by applying a voltage. Each electrode 114R, 114G, 114B connected to each stripes 112R, 112G, 112B is connected to a galvanic cell 11 through multiplexer 115 and another electrodes are commonly grounded. For example, in multiplexer 115 under the condition as shown in FIG. 13, each stripes 112R of liquid crystal panels 112 in contact with each red transmitting stripe 16R comprise the light transmitting stripes and the residual stripes 112G, 112B comprises the shutter stripes. Said multiplexer 115 is designed to be switched in synchronized with multiplexer 105 for video processor means 102. There will be now disclosed the functioning of the seventh embodiment constructed as mentioned above.

Multiplexers 115, 105 for illuminating means 113 and for video processor means 102 are gang controlled by the switching signals based on the clock signals from reference oscillator 107 so that multiplexer 105 is connected to red frame memory 106R during the interval required for sensing the signals issued from all of the receiver elements on solid-state image sensing element 4, for example under the condition that electrode 114R of multiplexer 115 is applied with the voltage of galvanic cell 116.

As liquid crystal panel 112 passes light only through each stripes as shown by the symbol 112R, light transmitted through each stripes 112R is incident only red transmitting stripes 16R in three color filter 16 to limit the light having red wave length by said stripes 16R and to illuminate the object through light guide 10.

Under the red illuminating light, the signals received by each receiver element of solid-state image sensing element 4 are amplified through preamplifier 5, A/D converted and stored successively to the memory cell in red frame memory 106R connected with multiplexer 105 and assigned by the address signals.

After the completion of signals received by all of the receiver elements in said solid-state image sensing element 4, multiplexer 115 is switched so that the voltage is applied to the stripes 112G which are contacted with green transmitting stripes 16G in liquid crystal panel 112 to illuminate the object with green light. At the same time, multiplexer 105 in video processor means 102 is connected to green frame memory 106G to turn said frame memory 106G to the writing mode to store successively the signals form the receiver elements similarly to the manner as mentioned above. In a similar manner, the object is eluminated by blue light passing through blue transmitting filter 16B and the signals from the receiver elements for one frame are stored in blue frame memory 106B. After the completion of writing to blue frame memory 106B, each frame memory 106R, 106G, 106B is turned to the reading mode at the same time and the sensed signals (data) are D/A converted to be restored each analogue color signals R, G, B and said color signals are passed through color amplifier 34R, 34G, 34B and color displayed on CRT 35 while being swept by horizontal and vertical deflection signals.

As seen from the above disclosure, the object can be illuminated with light having each color only by energizing and deenergizing successively each stripes 112R, 112G, 112B of liquid crystal panel 112 and sensed under the illumination of each color to store the image signals in frame memories 106R, 106G, 106B and to sense three color signals concurrent to be color displayed on CRT.

According to the seventh embodiment, the means include no movable member so that the constant performance can be maintained and high reliability can be sustained for a long period of time. Moreover, illuminating means 113 for the color image sensor can be provided by attaching liquid crystal panel 112 to three color filter 16 and controlling the application of voltage of galvanic cell 116 through multiplexer 115 or the like so that the inexpensive and miniaturized means can be provided. Furthermore, according to such illuminating means 113, the resolving power is not degraded by changing the monochromatic sensor to the polychromatic sensor and the information with various colors can be provided, so that a diseased portion or the like can be sensed or reproduced as a distinct colored image. Still further, the image can be displayed by mixing freely the different color image so as to diagnose more exactly. FIG. 16 illustrates the tip of insert member of endoscope according to the eighth embodiment of the present invention. In this eighth embodiment, said three color filter 16 and liquid crystal panel 112 are installed on the optical path between the incident end of light guide 10 and light distributing lens system 8, for example, at the pupillary position of light distributing lens system 8.

Said liquid crystal panel 112 is so structured that voltage can be applied selectively by way of lead wire bundle 114 to stripes 112R, 112G, 112B arranged in the confronted relation to each light transmitting stripes 16R, 16G, 16B of three color filter 16.

The eighth embodiment is constructed similarly to said seventh embodiment except that three color filter 16 and liquid crystal panel 112 are installed between condensor lens system 15 according to said seventh embodiment and an incandescent lamp 13 within the tip of insert member 2.

FIG. 17 illustrates the ninth embodiment of the present invention.

In this embodiment, light guide 10 as in the eighth embodiment is not employed and thus, illuminating lamp 13, etc. in light source means 111 as shown in FIG. 13 is eliminated, but a white incandescent lamp 121 is installed in the tip of insert member 2 and said three color filter 16 and liquid crystal panel 112 are installed on the optical path between said lamp 121 and light distributing lens system 8, for example, at the pulpillary position of the lens.

It is obvious that said lamp 121 may be replaced by high performance luminous diode(s) containing wave lengths of the three colors.

FIG. 18 illustrates the tenth embodiment of the present invention.

This embodiment is different from the seventh embodiment in that three color filter 16 and liquid crystal panel 112 are not attached between condensor lens system 15 and illuminating lamp 13, but contacted with a reflector.

Namely, three color filter 16 is bonded with the concave surface of concaved liquid crystal panel 112 in which portions applied with a voltage on the concave surface comprise reflective portions and residual portions comprise light transmitting portions or non-reflective portions.

When the light from illuminating lamp 13 is incident directly to the condensor lens system, a shutter disk may be provided between the lamp and the condensor lens system. This embodiment is advantageous in that no reflector 14 is required.

In the above-mentioned embodiments, the light transmitting portions and reflecting portions of three color filter 16 and liquid crystal panel 112 comprise stripes, but the invention should not be constructed to be limited to such stripes.

Moreover, as shown in the embodiment of FIG. 9, the color image sensor of successive color modes can be achieved by incorporating three color filter 16 and liquid crystal panel 112 at the pulpillary position of objective lens system 3.

It is obvious that embodiments differ within a wide range can be structured on the basis of this invention without departing from the spirit and scope of this invention. Thus, the present invention should not be limited by any particular embodiments except by the attached claim of this invention.

What is claimed is:

1. Color image sensing means of a sequential three color mode for an endoscope assembly, comprising:
   an elongated insert member;
   illuminating means having a light source for emitting illuminating light from the tip of said insert member;
   a solid-state image sensing element positioned at the tip of said insert member and incorporating an imaging optical system for focussing the image of an object, illuminated by said illuminating means, on an image sensing surface having a great number of receiver elements having photoelectric conversion properties positioned on the focal plane of said imaging optical system;
   video processor means for receiving the signals issued from said solid-state image sensing element and processing the signals by amplifying or the like to output the color signals at a predetermined timing;
   color displaying means for displaying the color signals supplied from said video processor means;
   filter means comprising a plurality of three color filters, and each color alternately arranged in the form of stripes arranged repeatedly at a predetermined pitch for transmitting each of said three colors of light therethrough, said filter means positioned in an optical path between said light source and said solid-state image sensing element;
   light transmitting means disposed proximal to said filter means and including light transmitting portions facing a group of said monochromatic filters for allowing light to pass therethrough and residual shutter portions for preventing light from passing therethrough;
   vibrator means for reciprocating said filter means with respect to said light transmitting means sequentially so as to shift said group of monochromatic filters to a subsequent group of monochromatic filters of another color with respect to said light transmitting portions; and
   driving means for supplying electrical signals for driving said vibrator means; thereby providing light to said solid-state image sensing means which has three different wave lengths successively by actuating said vibrator means.

2. Means according to claim 1 wherein the trailing end of light guide inserted through said insert member is provided with said filter means, light transmitting means and vibrator means.

3. Means according to claim 1 wherein said filter means, light transmitting means and vibrator means are positioned at the forward position from the tip of insert member emitting the illuminating light.

4. Means according to claim 1 wherein said filter means, light transmitting means and vibrator means are installed at the pupillary position of said imaging optical system.

5. Means according to claim 1 wherein said vibrator means comprise bi-morph vibrators.

6. Means according to claim 1 wherein said light transmitting means comprises a shutter disk provided with a number of openings in the form of slits.

7. Means according to claim 1 wherein said light transmitting means comprises a shutter disk provided with a plurality of openings in the form of slits and a plurality of cylindrical lens systems disposed proximal to at least one side of said shutter disk so as to increase the intensity of light passing through said openings.

8. Color image sensing means of a sequential three color image sensing mode for an endoscope assembly, comprising:

an elongated insert member;

illuminating means having a light source for emitting illumination light from the tip of said insert member;

an imaging optical system incorporated at the leading end of said insert member for focussing the image of an object illuminated by said illuminating means;

a solid-state image sensing element provided with an image sensing plane comprising a great number of receiver elements each having photoelectrical conversion properties and positioned on the focal plane of said imaging optical system;

video processor means for receiving the signals issued from said solid-state image sensing element and processing the signals by amplifying or otherwise to provide the color signals at a predetermined timing;

color displaying means for displaying the color signals supplied from said video processor means;

a filter means positioned in an optical path between said light source and said solid-state image sensing element and comprising a plurality of three color filters, each color alternately arranged in the form of stripes arranged repeatedly at a predetermined pitch for transmitting each of said three colors of light successively therethrough;

a liquid crystal panel arranged proximal to said filter means and wherein the portions facing one group of said color filter are transformable to light transmitting portions by applying voltage and remaining portions act as non-light transmitting shutter portions; and multiplexer means for turning the portions of liquid crystal panel facing each color filters to a light transmitting condition; thereby providing light having three different wave lengths to said solid-state image sensing element by switching the energization of each electrode on said liquid crystal panel for sensing multichromatically.

9. Means according to claim 8 wherein said filter means and liquid crystal panel are positioned in said illuminating means with the trailing end of light guide inserted through the insert member.

10. Means according to claim 1 wherein said filter means and liquid crystal panel are provided at a position forwards from the leading end of insert member.

11. Means according to claim 8 wherein said filter means and liquid crystal panel are provided at the pupillary position of said imaging optical system.

* * * * *